United States Patent
Luo et al.

(10) Patent No.: US 8,186,643 B2
(45) Date of Patent: May 29, 2012

(54) APPARATUS FOR ATTACHING A DEVICE TO A CIRCULAR STRUCTURE

(75) Inventors: Wei Luo, State College, PA (US);
Tounine Mayer, State College, PA (US);
Jae Choi, State College, PA (US)

(73) Assignee: General Electric Company, Schenectady, NY (US)

( * ) Notice: Subject to any disclaimer, the term of this patent is extended or adjusted under 35 U.S.C. 154(b) by 41 days.

(21) Appl. No.: 12/731,309

(22) Filed: Mar. 25, 2010

(65) Prior Publication Data

US 2011/0233377 A1    Sep. 29, 2011

(51) Int. Cl.
*F16M 11/00* (2006.01)

(52) U.S. Cl. .......... 248/689; 248/230.8; 248/230.9; 285/410; 269/131

(58) Field of Classification Search .......... 248/230.8, 248/689; 269/131; 285/410; 72/756
See application file for complete search history.

(56) References Cited

U.S. PATENT DOCUMENTS

| | | | |
|---|---|---|---|
| 812,625 A | | 2/1906 | Weston |
| 1,848,527 A | * | 3/1932 | Hickey ............ 269/131 |
| 2,379,014 A | * | 6/1945 | Lowe ............ 24/116 R |
| 2,524,436 A | * | 10/1950 | Evans et al. ............ 248/230.8 |
| 2,968,978 A | * | 1/1961 | Wheeler ............ 269/130 |
| 3,480,270 A | * | 11/1969 | Gill ............ 269/131 |
| 3,525,158 A | * | 8/1970 | Torlay ............ 33/661 |
| 3,593,402 A | * | 7/1971 | Mori ............ 29/256 |
| 3,664,029 A | * | 5/1972 | Glucoft et al. ............ 33/572 |
| 3,704,503 A | * | 12/1972 | Haywood ............ 29/256 |
| 4,016,637 A | * | 4/1977 | Swensen ............ 29/281.4 |
| 4,094,612 A | * | 6/1978 | Krieg ............ 408/92 |
| 4,242,744 A | | 12/1980 | Rottmar |
| 4,244,111 A | * | 1/1981 | Heard, Sr. ............ 33/572 |

(Continued)

FOREIGN PATENT DOCUMENTS

DE    102004052489 A1    5/2006

(Continued)

OTHER PUBLICATIONS

Baltzersen, Øystein; Solstad, Arne; Daaland, Alf; and Holberg, Jens Kristian; "Multichannel Ultrasonic Monitoring of Corrosion on Subsea Pipelines", NDT.net, Jun. 2005, vol. 10, No. 6 (8 pgs).

(Continued)

*Primary Examiner* — Terrell McKinnon
*Assistant Examiner* — Daniel J Breslin
(74) *Attorney, Agent, or Firm* — GE Global Patent Operation; Mark A. Conklin

(57) ABSTRACT

An apparatus for attaching a device to a circular structure is disclosed. In one embodiment, the apparatus includes a clamp body attached to the outer surface of the circular structure using a strap, which can be attached to the clamp body using a spring that maintains an attachment force to prevent movement of the clamp body over a wide range of temperatures and temperature cycling of the circular structure and the strap. In one embodiment, the device can be installed in the clamp body and coupled to the outer surface of the circular structure using one or more spring washers that maintain an attachment force between the device and the outer surface of the circular structure to prevent detachment of the device from the outer surface of the circular structure over a wide range of temperatures and temperature cycling of the circular structure.

19 Claims, 4 Drawing Sheets

U.S. PATENT DOCUMENTS

| | | | | |
|---|---|---|---|---|
| 4,282,730 | A * | 8/1981 | Lipschutz | 70/184 |
| 4,309,263 | A * | 1/1982 | Boyd | 204/196.17 |
| 4,348,000 | A * | 9/1982 | Hanner | 248/230.9 |
| 4,423,556 | A * | 1/1984 | DiVelez | 33/501 |
| 4,569,497 | A | 2/1986 | Elmer | |
| 4,595,487 | A | 6/1986 | Nunlist | |
| 4,726,575 | A * | 2/1988 | Dearman | 269/43 |
| 4,844,396 | A * | 7/1989 | Norton | 248/230.8 |
| 5,135,208 | A * | 8/1992 | Diskin | 269/130 |
| 5,329,673 | A | 7/1994 | Mason | |
| 5,782,561 | A * | 7/1998 | Pai | 374/151 |
| 6,264,406 | B1 * | 7/2001 | Bowles et al. | 408/92 |
| 6,641,124 | B2 * | 11/2003 | Melanson | 269/43 |
| 7,290,805 | B2 * | 11/2007 | Wu | 285/365 |
| 7,336,202 | B2 | 2/2008 | Kawai et al. | |
| 7,395,720 | B2 | 7/2008 | Wiest et al. | |
| 2006/0170215 | A1 * | 8/2006 | Cousineau | 285/420 |
| 2008/0148862 | A1 | 6/2008 | Aikens | |

FOREIGN PATENT DOCUMENTS

| | | |
|---|---|---|
| FR | 2404202 A1 | 4/1979 |
| GB | 2021677 A | 12/1979 |
| JP | 10-300708 A | 11/1998 |

OTHER PUBLICATIONS

Search Report from corresponding EP Application No. 11159289.5-1252 dated Jul. 18, 2011.

* cited by examiner

APPARATUS FOR ATTACHING A DEVICE TO A CIRCULAR STRUCTURE

BACKGROUND OF THE INVENTION

The subject matter disclosed herein relates to an apparatus for attaching a device to the outer surface of a circular structure, and more particularly, to an apparatus for coupling a nondestructive testing device to the outer surface of a pipe.

Several industries (e.g., oil and gas, refinery, chemical, power generation) require the transport of fluid (e.g., liquids or gases) through pipes. Nondestructive testing devices can be placed on the outer surface of these pipes to monitor corrosion/erosion of the pipes, including corrosion/erosion on the interior of pipe walls. In many cases, the probe or other nondestructive testing device is permanently coupled to the outer surface of the pipe at a single location to continuously monitor corrosion/erosion at that location to determine pipe corrosion/erosion rates and to determine whether that pipe location is in need of preventative maintenance to prevent a pipe failure.

One example of a nondestructive testing device used to monitor corrosion/erosion of a pipe is an ultrasonic testing device. When conducting ultrasonic testing of a pipe, an ultrasonic pulse is emitted from a probe coupled to the outer surface of the pipe and passed through the pipe wall. As the ultrasonic pulse passes into and through the pipe wall, various pulse reflections called echoes are reflected back to the probe as the pulse interacts with the outer surface of the pipe, internal structures within the pipe wall, and with the back wall of the pipe wall. The echo signals can be displayed on a screen with echo amplitudes appearing as vertical traces and time of flight or distance as horizontal traces. By tracking the time difference between the transmission of the ultrasonic pulse and the receipt of the echoes, various characteristics of the pipe can be determined, including pipe wall thickness. If the thickness of the pipe wall at the location of the ultrasonic testing device decreases over time (e.g., as would be shown be a reduction in the time of flight of the back wall echo), this can be an indication of corrosion/erosion.

Since much of the analysis in ultrasonic testing, as well as other nondestructive testing techniques (e.g., electromagnetic, infrared/thermal, radiographic, etc.), is based on comparisons of current measurements to past measurements or to known measurements based on calibration or original dimensions, it is necessary to ensure that the position and coupling of the probe in relation to the outer surface of the pipe remain fixed and unchanged over time. For example, if the probe remains coupled to the outer surface of the pipe but moves along the outer surface of the pipe from one location to another, this can lead to inaccurate results based on the comparison of data from two different locations on the outer surface of the pipe. Similarly, if the probe becomes decoupled from the outer surface of the pipe or the coupling force between the probe and the outer surface of the pipe changes, this can result to inaccurate results based on the comparison of data from different coupling positions on the outer surface of the pipe or different coupling forces. For instance, if the probe was not properly coupled to the outer surface of the pipe, this could lead to inaccurate time of flight data that would fail to accurately indicate the amount of corrosion/erosion at a location of the pipe. In some cases, the decoupling could be so significant that it would prevent the ability of the probe to transmit the ultrasonic pulse through the pipe wall to conduct any testing.

One existing solution for coupling a probe or other nondestructive testing device to the outer surface of a pipe is a metal clamp that includes a U-bolt fastened to a clamp body, wherein the bend of the U-bolt is fitted around one side (e.g., the bottom) of the outer surface of the pipe and the threaded ends of the U-bolt are fastened to the clamp body that extends from one threaded end of the U-bolt to the other across the opposite side (e.g., the top) of the outer surface of the pipe. In some installations where a probe is required on opposite sides of the pipe, rather than use a U-bolt, conventional bolts can attach one clamp body on one side of the pipe to another clamp body on the opposite side of the pipe. Since the clamp bodies, U-bolts, and/or bolts used in this existing metal clamp are sized based on the outer diameter of the outer surface of the pipe (e.g., in the range of 2" (50.8 mm) to 40" (1,016 mm)), a single metal clamp design can typically only be used for two or three different sized pipes (e.g., one metal clamp can only be used for 6" (152.4 mm), 8" (203.2 mm), and 10" (254 mm) pipes). Also, given the configuration of the existing metal clamp, a single metal clamp design can typically only be used to accommodate one or two probes on the circumference of the outer surface of the pipe at a particular location (e.g., on the top and bottom of the pipe, but not on the sides, or on the left side and right side of the pipe, but not on the top and bottom).

In the existing bolt or U-bolt metal clamp, the portion of the clamp body contacting the outer surface of the pipe can include an opening into which the probe can be installed. In some installations, a metal block is placed over the cavity after the probe is installed in the cavity. One or more bolts can then be tightened to apply force down onto the probe until the desired coupling force between the probe and the outer surface of the pipe is achieved. While this existing bolt or U-bolt metal clamp is capable in some cases of ensuring that the position and coupling of the probe in relation to the outer surface of the pipe remain fixed and unchanged over time, there can be circumstances where this is not the case. For example, the use of multiple bolts on the clamp body to establish the desired coupling force introduces the possibility that, if one bolt is tightened more than another, certain parts of the probe may be coupled to the outer surface of the pipe at different coupling forces than other parts of the probe.

Changes in temperature of the existing clamp and the pipe over time can also result in changes in the position and coupling of the probe in relation to the pipe by changing the shape of the metal clamp and the pipe. For example, if the fluid being transported through the pipe is at a high temperature (e.g., greater than 350° C.), the pipe can be heated to this high temperature, resulting in thermal expansion of the pipe (i.e., increase in the outer diameter of the pipe), which may bend or otherwise deform the clamp body or U-bolts/bots of the existing metal clamp. In addition, if the pipe is heated to this high temperature, the existing metal clamp, which is in contact with the outer surface of the pipe, can also be heated to this high temperature, making the existing metal clamp more malleable and likely to bend or otherwise deform. To the extent that the pipe and existing metal clamp are made of different materials (e.g., stainless steel, carbon steel), the effect of the high temperature on the pipe and existing metal clamp may differ (e.g., different amounts and rates of thermal expansion and contraction). Even if the pipe and existing metal clamp are made of the same material, the effect of the high temperature on the pipe and existing metal clamp may differ based on the different ambient conditions of the pipe and the existing metal clamp. The continuous temperature cycling (e.g., thermal expansion and contraction) of the pipe and the existing metal clamp can result in changes in the position and coupling of the probe in relation to the pipe. In some cases, the temperature cycling may be so significant over time that the probe becomes decoupled from the outer surface of the pipe, requiring that the existing metal clamp be removed and replaced in a laborious process. In order to minimize temperature cycling, the size and thickness of the existing metal clamp can be significantly increased, which increases the difficulty of handling and installing the clamp and undesirably increases the weight of the clamp on the pipe.

It would be advantageous to provide an apparatus for attaching a device to the outer surface of a pipe that does not have the disadvantages associated with the existing metal clamp.

BRIEF DESCRIPTION OF THE INVENTION

An apparatus for attaching a device to a circular structure is disclosed. In one embodiment, the apparatus includes a clamp body attached to the outer surface of the circular structure using a strap, which can be attached to the clamp body using a spring that maintains an attachment force to prevent movement of the clamp body over a wide range of temperatures and temperature cycling of the circular structure and the strap. In one embodiment, the device can be installed in the clamp body and coupled to the outer surface of the circular structure using one or more spring washers that maintain an attachment force between the device and the outer surface of the circular structure to prevent detachment of the device from the outer surface of the circular structure over a wide range of temperatures and temperature cycling of the circular structure.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of invention. Thus, for further understanding of the invention, reference can be made to the following detailed description, read in connection with the drawings in which.

DETAILED DESCRIPTION OF THE INVENTION

Figure 1:
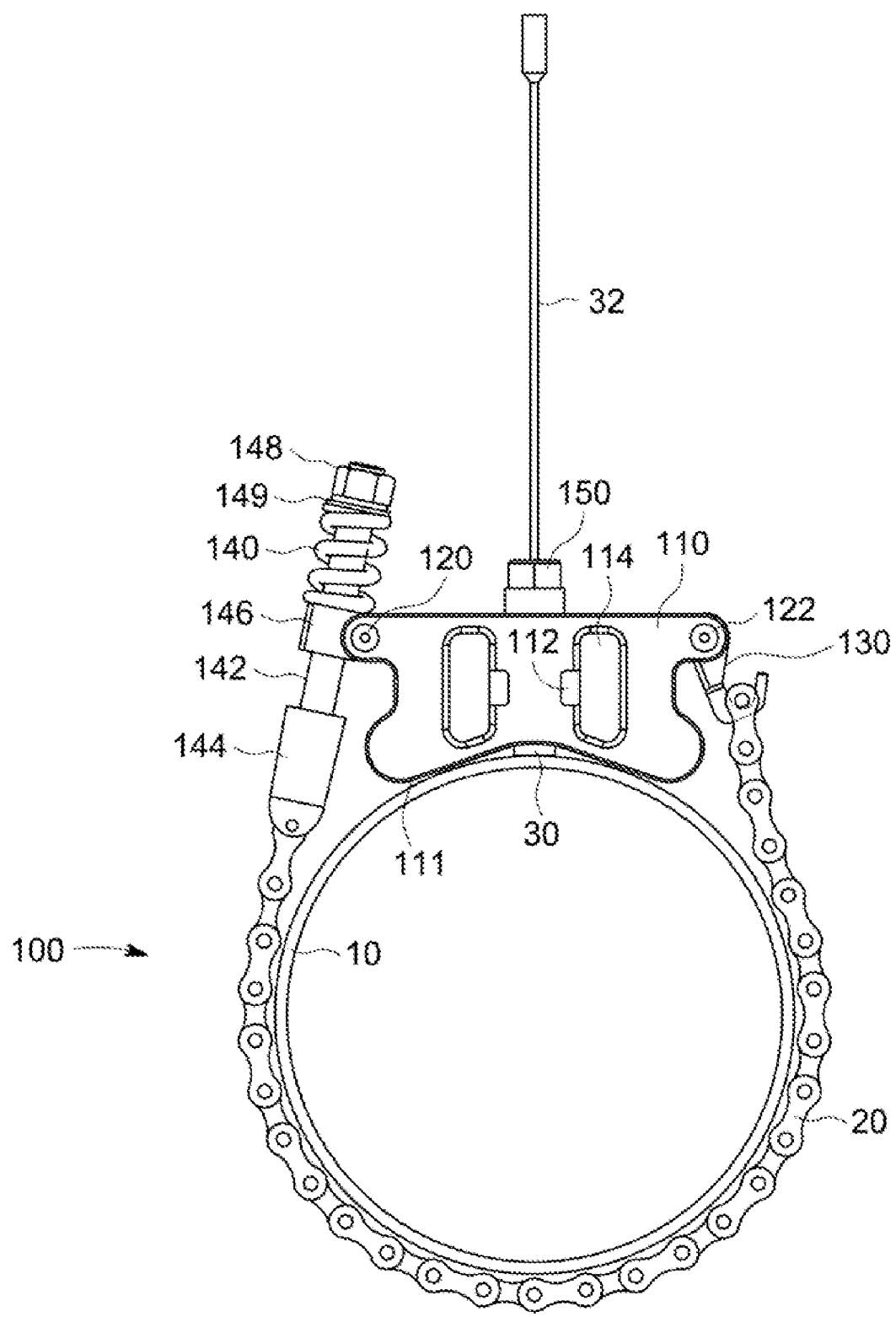
FIG. 1 shows a clamp for coupling a probe to the outer surface of a pipe in an exemplary embodiment of the invention.

FIG. 1 shows a clamp 100 for attaching (e.g., coupling) a probe 30 to the outer surface of a pipe 10 (e.g., having an outer diameter of 10" (254 mm)) in an exemplary embodiment of the invention. Although the exemplary embodiment of the clamp is shown coupling a probe 30 to the outer surface of a pipe 10, the clamp 100 can be used to attach a variety of devices to a variety of circular structures besides probes 30 or other nondestructive testing devices, and besides pipes (e.g., other conduits, poles, etc.). As shown in FIG. 1, the probe 30 and associated probe wire 32 can be installed within a clamp body 110, which can couple the probe 30 to the outer surface of the pipe 10. In one embodiment, the clamp body 110 can include a clamp body opening 116 (e.g., a hole) to receive and hold the probe 30 against the outer surface of the pipe 10. The probe 30 can be coupled to the outer surface of the pipe 10 through an acoustically conductive foil (not shown) (e.g., a gold foil) or other conductive material.

Figure 2:
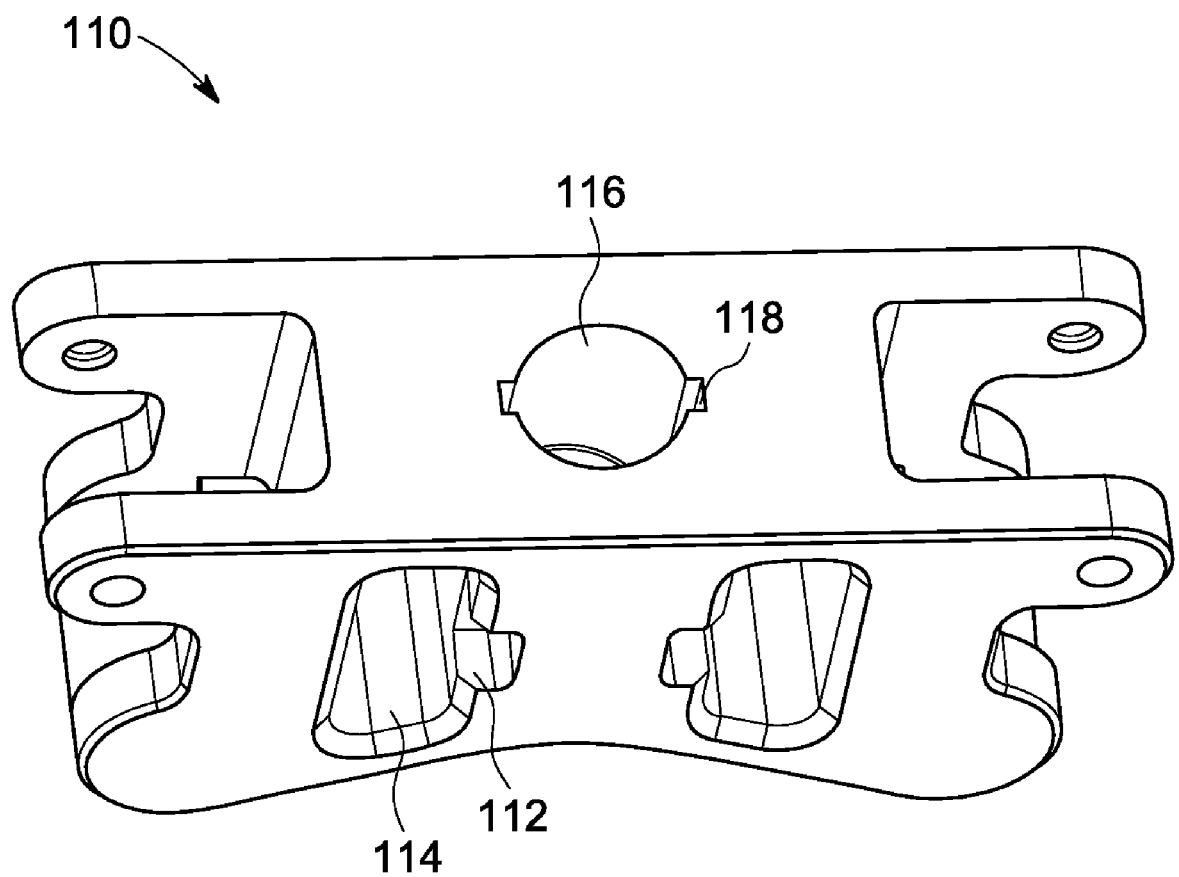
FIG. 2 shows a perspective view of the clamp body shown in FIG. 1 in an exemplary embodiment of the invention.

FIG. 2 shows a perspective view of the clamp body 110 shown in FIG. 1 in an exemplary embodiment of the invention. In one embodiment, the clamp body 110 can be made of 303 stainless steel. The clamp body 110 can include transverse openings 114 to reduce the weight of the clamp body 110 and to make the clamp body 110 easier to handle during installation. The clamp body 100 can also include a clamp body opening 116 that includes clamp body opening longitudinal slots 118 into which the probe 30 can be installed.

Figure 3:
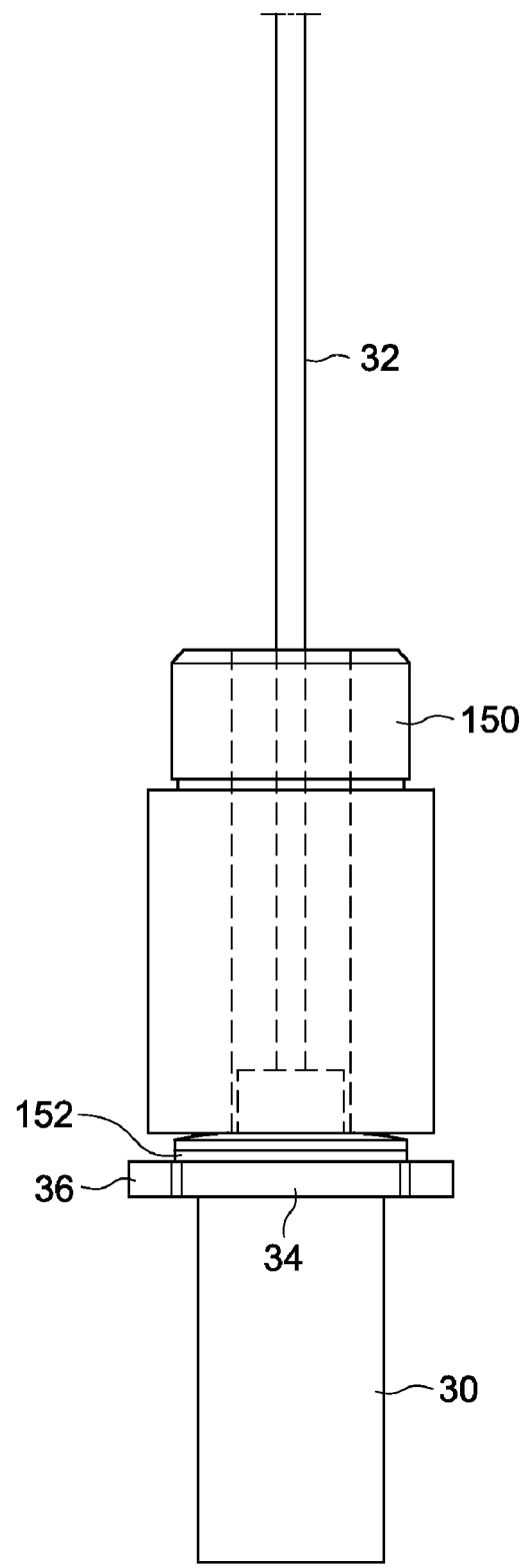
FIG. 3 shows the portion of the probe installed in the clamp body shown in FIG. 1 in an exemplary embodiment of the invention.

FIG. 3 shows the portion of the probe 30 installed in the clamp body 110 shown in FIG. 1 in an exemplary embodiment of the invention. The backside of the probe 30 can be held by a probe ring 34 with probe ring tabs 36 that slide into the clamp body opening 116 and clamp body opening longitudinal slots 118 when the probe 30 is inserted into the clamp body 110 shown in FIG. 2. In many installations, a certain coupling force (e.g., 1,000 lbs) or a range of coupling forces is necessary to ensure a proper coupling between the probe 30 and the outer surface of the pipe 10. A pushing nut 150 through which the probe cable 32 can pass can be threaded into a threaded portion of the clamp body opening 116 to apply force down onto the probe 30 through the probe ring 34 until the desired coupling force between the probe 30 and the outer surface of the pipe 10 is achieved. In one embodiment shown in FIG. 3, the pushing nut 150 comprises a hexagonal nut on top of a cylindrical body, at least a portion of which is threaded. As shown in FIG. 3, one or more spring washers 152 (also referred to as cupped spring washers, Belleville washers, Belleville springs, or coned-disk springs) can be installed between the pushing nut 150 and the probe ring 34 in the clamp body opening 116 to apply the desired coupling force to the probe 30. For example, if a coupling force of 1,000 lbs. is required and each spring washer 152 is rated to provide 700 lbs. of force, two spring washers 152 can be used. During installation, calibration and other testing can be performed to confirm that the actual coupling force between the probe 30 and the outer surface of the pipe 10 is within the acceptable range of coupling forces.

After installation, the spring washers 152 can maintain the required coupling force between the probe 30 and the outer surface of the pipe 10 within an acceptable range even if the outer diameter of the pipe 10 changes based on changes in temperature or other factors. For example, without the spring washers 152, if the temperature of the pipe 10 decreased such that the outer diameter of the pipe 10 also decreased, the coupling force between the probe 30 and the outer surface of the pipe 10 would decrease as the outer surface of pipe 10 moved away from the probe 30. However, in the inventive clamp 100, the spring washers 152 can expand as the outer surface of pipe 10 moves away from the probe 30 to press down on the probe 10 to maintain the required coupling force between the probe 30 and the outer surface of the pipe 10 to prevent movement of the probe 30 away from the outer surface of the pipe 10.

As the pushing nut 150 is threaded down onto the probe ring 34 and the probe 30, the probe ring tabs 36 received by the clamp body opening longitudinal slots 118 prevent the probe 30 from rotating with the pushing nut 150. As shown in FIG. 2, the clamp body 110 can include two clamp body wrench slots 112 to receive a wrench used to prevent the clamp body 110 from rotating with the pushing nut 150. These features can prevent the probe 30 from twisting against the outer surface of the pipe 10 during the threading of the pushing nut 150 down into the clamp body opening 116 and damaging the delay of the probe 30 or the foil that may be installed between the probe 30 and the outer surface of the pipe 10.

Figure 4:
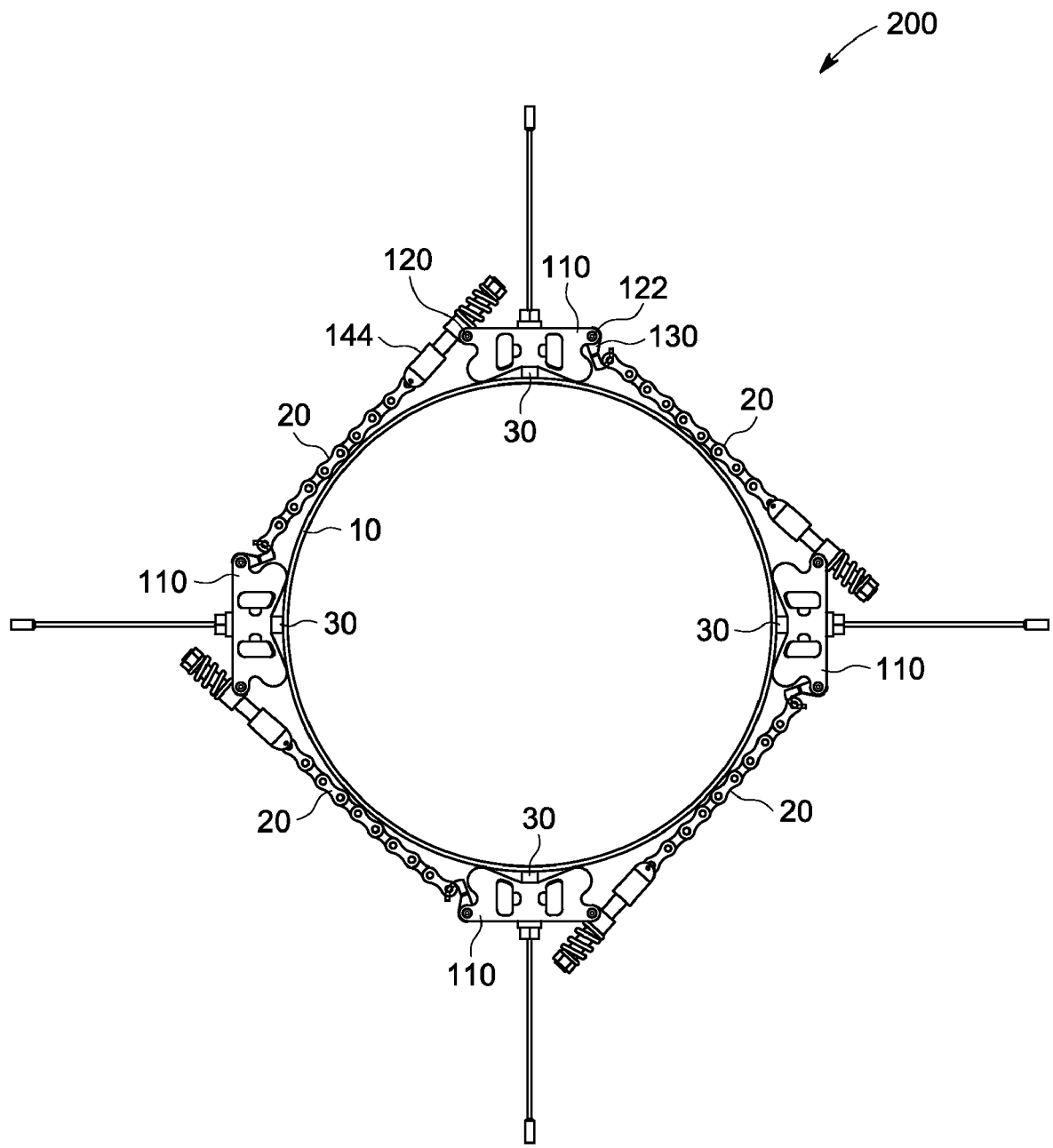
FIG. 4 shows a multi-probe clamp for coupling a plurality of probes to the outer surface of a pipe in an exemplary embodiment of the invention.

The bottom surface 111 of the clamp body 110 is configured (e.g., curved) to rest on the outer surface of pipes 10 over a wide range of outer diameters. For example, the radius of curvature of the clamp body bottom surface 111 can be designed to be substantially the same as the radius of curvature of the outer surface of the smallest diameter pipe 10 that the clamp body 110 may be used with. Similarly, the radius of curvature of the clamp body bottom surface 111 can be designed so that the ends of the bottom surface 111 contact the outer surface of the largest diameter pipe 10 that the clamp body 110 may be used with while allowing the probe 30 to extend far enough below the clamp body bottom surface 111 to couple with the outer surface of the pipe 10 (as shown in FIG. 4 for the pipe having a larger outer diameter (e.g., 20" (508 mm)).

Returning to FIG. 1, the clamp body 110 is attached to the outer surface of the pipe 10 using a strap 20 placed on the circumference of the outer surface of the pipe 10. In the exemplary embodiment shown in FIG. 1, the strap 20 used to attach a single clamp body 110 to the outer surface of the pipe 10 is a roller chain, similar to a chain used on a bicycle. In one embodiment, the strap 20 can be made of carbon steel. Other straps 20 (e.g., cables, ropes, other types of chains, etc.) can be also be used. In one embodiment, the strap 20 can be coated to prevent corrosion on the strap 20 and the outer surface of the pipe 10 contacted by the strap 20. The flexibility provided by the design of the clamp body 110 and the strap 20 allows a single clamp 100 to be used on pipes 10 over a wide range of outer diameters by adjusting the length of the strap 20. In an embodiment including a plurality of clamp bodies 110 (see FIG. 4), a plurality of straps 20 can be used to join the clamp bodies 110

In one embodiment, on one end of the clamp body 110, a hook 130 or other fastener can be attached for fastening the clamp body 110 to the strap 20. In the case where the strap 20 is a chain or other linked structure, one of the links in the chain can be slid over the hook 130 or fixedly fastened to the hook 130. In the exemplary embodiment shown in FIG. 1, the hook 130 is pivotally attached to the clamp body 110 by a hook pivot 122 that can rotate to provide the appropriate angle of connection to the strap 20 determined by the outer diameter of the pipe 10. For example, the angle of the hook 130 provided by the hook pivot 122 for the smaller pipe shown in FIG. 1 is smaller than the angle of the hook 130 provided by the hook pivot 122 for the larger pipe shown in FIG. 4. The configuration of the hook 130 and hook pivot 122 can be varied to suit different applications, including the use of a bolt arm pivoting on the clamp body 110, a bolt extending through the bolt arm with a hook on the end of it to attach to the strap 20, and a nut at the opposite end of the hook.

In one embodiment, on the other end of the clamp body 110, a bolt 142 can be attached for connecting the clamp body 110 to the strap 20. In the exemplary embodiment shown in FIG. 1, the bolt 142 extends through a bolt arm 146. One end of the bolt 142 can extend through and below the bolt arm 146 and can be threaded into, or otherwise attached, to a strap arm 144 that is fastened to the strap 20. The bolt arm 146 is pivotally attached to the clamp body 110 by a bolt arm pivot 120 that can rotate to provide the appropriate angle of connection to the strap 20 determined by the outer diameter of the pipe 10. For example, the angle of the strap arm 144 provided by the bolt arm pivot 120 for the smaller pipe shown in FIG. 1 is smaller than the angle of the strap arm 144 provided by the bolt arm pivot 120 for the larger pipe shown in FIG. 4. In the case where the strap 20 is a chain or other linked structure, one of the links in the chain can be slid over the strap arm 144 or fixedly fastened to the strap arm 144. The other end of the bolt 142 can extend through and above the bolt arm 146 for a sufficient distance to allow for the installation of a compression coil spring 140 or other spring between the bolt arm 146 and a nut 148 on the end of the bolt 142. In one embodiment, one or more washers 149 can be used to distribute the load between the nut 148 and the compression coil spring 140. In one embodiment used for a range of larger diameter pipes, the compression coil spring 140 can be a 2" (50.8 mm) long spring that can be compressed a maximum of approximately 0.5" (12.7 mm) under a load of 1,500 lbs. For smaller diameter pipes, the compression coil spring 140 can be chosen to withstand a smaller load (e.g., 700 lbs).

During installation of the clamp body 110 onto the outer surface of the pipe 10, after the appropriate lengths of straps 20 have been attached to the clamp body 110, the nut 148 can be tightened down onto the bolt 142 by compressing the compression coil spring 140 to a point between its fully extended position (0.0" (0 mm)) and its fully compressed position (0.5" (12.7 mm)) (e.g., 0.25" (6.35 mm)). As the compression coil spring 140 is compressed, it exerts an upward force on the nut 148 (or washers 149), which exerts an upward force on the bolt 142 and attached strap arm 144, increasing the tension on the strap 20 attached to the outer surface of the pipe 10, and thereby increasing the attachment force between the clamp body 110 and the outer surface of the pipe 10 provided by the strap 20.

After installation, the compression coil spring 140 can maintain the attachment force between the clamp body 110 and the outer surface of the pipe 10 provided by the strap 20 within an acceptable range even if the outer diameter of the pipe 10 or the strap 20 changes based on changes in temperature or other factors, including circumstances where the outer diameter of the pipe 10 or the strap 20 change at different rates. For example, without the compression coil spring 140, if the temperature of the pipe 10 decreased such that the outer diameter of the pipe 10 also decreased at a different rate than the strap 20, the attachment force between the clamp body 110 and the outer surface of the pipe 10 provided by the strap 20 would decrease as there would be more slack in the strap 20. This may cause relative movement between the probe 30 and the outer surface of the pipe 10 that may result in decoupling of the probe 30 from the outer surface of the pipe 10. However, in the inventive clamp 100, the compressed coil spring 140 can expand as the outer diameter of the pipe 10 thermally contracts, exerting an upward force on the nut 148 (or washers 149), which exerts an upward force on the bolt 142 and attached strap arm 144, maintaining sufficient attachment force between the clamp body 110 and the outer surface of the pipe 10 provided by the strap 20 to prevent movement of the clamp body 110 along the outer surface of the pipe 10. Similarly, without the compression coil spring 140, if the temperature of the pipe 10 increased such that the outer diameter of the pipe 10 also increased at a different rate than the strap 20, the attachment force between the clamp body 110 and the outer surface of the pipe 10 provided by the strap 20 might increase as there would be increased force on the strap 20. The increase in force could be significant enough to damage the strap 20 and the probe 30. However, in the inventive clamp 100, the compressed coil spring 140 can contract as the outer diameter of the pipe 10 expends, allowing the bolt 142 and attached strap arm 144 to extend downward, decreasing the tension of the strap 20 attached to the outer surface of the pipe 10 to maintain sufficient attachment force between the clamp body 110 and the outer surface of the pipe 10 provided by the strap 20 to prevent movement of the clamp body 110 along the outer surface of the pipe 10.

FIG. 4 shows a multi-probe clamp 200 for coupling a plurality of probes 30 to the outer surface of a pipe 10 having an outer diameter of 20" (508 mm)) in an exemplary embodiment of the invention. While existing bolt or U-bolt metal clamp designs can only accommodate one or two probes 30 on the circumference of the outer surface of a pipe 10 at a particular location (e.g., on the top and bottom of the pipe, but not on the sides, or on the left side and right side of the pipe, but not on the top and bottom), the inventive clamp 100 can accommodate at least four probes 30 joined together by a plurality of straps 20 placed on the circumference of the outer surface of a pipe 10. The ability to accommodate more probes 30 increases the reliability of corrosion/erosion monitoring as different areas of pipes 10 (i.e., top, bottom, left side, right side) experience different amounts of corrosion/erosion.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An apparatus for attaching a device to a circular structure, wherein the apparatus comprises:
   a clamp body having a first end and a second end and comprising a first opening configured to receive the device, wherein the bottom surface of the clamp body is configured to rest on the outer surface of the circular structure;
   pivots extending through the clamp body at the first end and the second end, the pivots including a first pivot to pivotally attach a first fastener to the first end and a second pivot to pivotally attach a bolt arm to the second end;
   a bolt extending through the bolt arm and perpendicular to the second pivot, the bolt having a first end below the bolt arm and the second pivot and a second end above the bolt arm and the second pivot;
   a second fastener attached to the first end of the bolt;
   a nut attached to the second end of the bolt;
   one or more straps configured to be placed on the circumference of the outer surface of the circular structure, wherein a first end of the one or more straps is fastened to the first fastener and a second end of the one or more straps is fastened to the second fastener;
   a spring compressed between the nut and the bolt arm, wherein the spring maintains an attachment force between the clamp body and the outer surface of the circular structure provided by the one or more straps to prevent movement of the clamp body along the outer surface of the circular structure;
   a pushing nut in the first opening for applying force on the device until the device is attached to the outer surface of the circular structure; and
   a spring washer in the first opening between the pushing nut and the device, wherein the spring washer maintains an attachment force between the device and the outer surface of the circular structure provided by the pushing nut to prevent detachment of the device from the outer surface of the circular structure.

2. The apparatus of claim 1, wherein the clamp body further comprises a plurality of wrench slots to receive a wrench to prevent the clamp body from rotating with the pushing nut.

3. The apparatus of claim 1, wherein the clamp body further comprises a second opening to reduce the weight of the clamp body and to make the clamp body easier to handle during installation.

4. The apparatus of claim 1, wherein the one or more straps are chains.

5. The apparatus of claim 1, wherein the first fastener is a hook.

6. The apparatus of claim 1, wherein the pushing nut comprises a hexagonal nut on top of a cylindrical body.

7. The apparatus of claim 1, wherein the circular structure is a pipe.

8. The apparatus of claim 1, wherein the device is a non-destructive testing probe.

9. An apparatus for attaching a device to a circular structure, wherein the apparatus comprises:
   a clamp body comprising a first opening configured to receive the device, wherein the bottom surface of the clamp body is configured to rest on the outer surface of the circular structure;
   one or more straps configured to be placed on the circumference of the outer surface of the circular structure, wherein a first end of the one or more straps is fastened to a first fastener attached to a first end of the clamp body and a second end of the one or more straps is fastened to a second fastener;
   a bolt extending through a bolt arm attached to a second end of the clamp body, wherein the first end of the bolt below the bolt arm is attached to the second fastener and the second end of the bolt above the bolt arm is attached to a nut;
   a spring compressed between the nut and the bolt arm, wherein the spring maintains an attachment force between the clamp body and the outer surface of the circular structure provided by the one or more straps to prevent movement of the clamp body along the outer surface of the circular structure;
   a pushing nut in the first opening for applying force on the device until the device is attached to the outer surface of the circular structure;
   a spring washer in the first opening between the pushing nut and the device, wherein the spring washer maintains an attachment force between the device and the outer surface of the circular structure provided by the pushing nut to prevent detachment of the device from the outer surface of the circular structure; and
   a ring between the device and the spring washer for holding the backside of the device,
   wherein the ring further comprises a tab and wherein the first opening further comprises a longitudinal slot for receiving the tab of the ring to prevent the device from rotating with the pushing nut.

10. The apparatus of claim 9, wherein the clamp body further comprises a plurality of wrench slots to receive a wrench to prevent the clamp body from rotating with the pushing nut.

11. The apparatus of claim 9, wherein the bolt arm is pivotally attached to the second end of the clamp body.

12. The apparatus of claim 9, wherein the first fastener is a hook pivotally attached to the first end of the clamp body.

13. The apparatus of claim 9, wherein the pushing nut comprises a hexagonal nut on top of a cylindrical body.

14. An apparatus for attaching a device to a circular structure, wherein the apparatus comprises:
- a clamp body comprising a first opening configured to receive the device, wherein the bottom surface of the clamp body is configured to rest on the outer surface of the circular structure;
- one or more straps configured to be placed on the circumference of the outer surface of the circular structure, wherein a first end of the one or more straps is fastened to a first fastener attached to a first end of the clamp body and a second end of the one or more straps is fastened to a second fastener attached to a second end of the clamp body;
- a pushing nut in the first opening for applying force on the device until the device is attached to the outer surface of the circular structure;
- a spring washer in the first opening between the pushing nut and the device, wherein the spring washer maintains an attachment force between the device and the outer surface of the circular structure provided by the pushing nut to prevent detachment of the device from the outer surface of the circular structure; and
- a ring between the device and the spring washer for holding the backside of the device,
- wherein the ring further comprises a tab and wherein the first opening further comprises a longitudinal slot for receiving the tab of the ring to prevent the device from rotating with the pushing nut.

15. The apparatus of claim 14, wherein the clamp body further comprises a plurality of wrench slots to receive a wrench to prevent the clamp body from rotating with the pushing nut.

16. The apparatus of claim 14, wherein the clamp body further comprises a second opening to reduce the weight of the clamp body and to make the clamp body easier to handle during installation.

17. The apparatus of claim 14, wherein the one or more straps are chains.

18. The apparatus of claim 14, wherein the first fastener is a hook pivotally attached to the first end of the clamp body.

19. The apparatus of claim 14, wherein the pushing nut comprises a hexagonal nut on top of a cylindrical body.

* * * * *